US011580381B2

(12) United States Patent
Daval Frerot et al.

(10) Patent No.: US 11,580,381 B2
(45) Date of Patent: Feb. 14, 2023

(54) COMPLEX-VALUED NEURAL NETWORK WITH LEARNABLE NON-LINEARITIES IN MEDICAL IMAGING

(71) Applicant: Siemens Healthcare GmbH, Erlangen (DE)

(72) Inventors: Guillaume Daval Frerot, Lawrenceville, NJ (US); Xiao Chen, Princeton, NJ (US); Simon Arberet, Princeton, NJ (US); Boris Mailhe, Plainsboro, NJ (US); Mariappan S. Nadar, Plainsboro, NJ (US); Peter Speier, Erlangen (DE); Mathias Nittka, Baiersdorf (DE)

(73) Assignee: Siemens Healthcare GmbH, Erlangen (DE)

( * ) Notice: Subject to any disclaimer, the term of this patent is extended or adjusted under 35 U.S.C. 154(b) by 965 days.

(21) Appl. No.: 16/394,507

(22) Filed: Apr. 25, 2019

(65) Prior Publication Data
US 2020/0042873 A1 Feb. 6, 2020

Related U.S. Application Data

(60) Provisional application No. 62/713,135, filed on Aug. 1, 2018.

(51) Int. Cl.
*G16H 50/70* (2018.01)
*G06N 3/08* (2023.01)
*G06N 20/00* (2019.01)

(52) U.S. Cl.
CPC ............... *G06N 3/08* (2013.01); *G06N 20/00* (2019.01); *G16H 50/70* (2018.01)

(58) Field of Classification Search
CPC .......... G06N 3/08; G06N 20/00; G16H 50/70
See application file for complete search history.

(56) References Cited

U.S. PATENT DOCUMENTS

2019/0378311 A1* 12/2019 Mailhe .................. G06N 3/088

OTHER PUBLICATIONS

A. Moreau, et al. "Deep transform networks for scalable learning of MR reconstruction." Siemens Healthineers, Medical Imaging Technologies, Princeton, NJ, USA (2018).
Cocosco, Chris A., et al. "Brainweb: Online interface to a 3D MRI simulated brain database." NeuroImage. 1997.
Trabelsi, Chiheb, et al. "Deep complex networks." arXiv preprint arXiv:1705.09792 (2017).
Kim, Taehwan, and Tülay Adali. "Fully complex multi-layer perceptron network for nonlinear signal processing." Journal of VLSI signal processing systems for signal, image and video technology 32.1-2 (2002): 29-43.

(Continued)

*Primary Examiner* — Truong V Vo

(57) ABSTRACT

For machine training and application of a trained complex-valued machine learning model, an activation function of the machine learning model, such as a neural network, includes a learnable parameter that is complex or defined in a complex domain with two dimensions, such as real and imaginary or magnitude and phase dimensions. The complex learnable parameter is trained for any of various applications, such as MR fingerprinting, other medical imaging, or non-medical uses.

20 Claims, 9 Drawing Sheets

(56) References Cited

OTHER PUBLICATIONS

Mandic, Danilo P. "Complex valued recurrent neural networks for noncircular complex signals." 2009 International Joint Conference on Neural Networks. IEEE, 2009.
Savitha, Ramaswamy, Sundaram Suresh, and N. Sundararajan. "A fully complex-valued radial basis function network and its learning algorithm." International Journal of Neural Systems 19.04 (2009): 253-267.
Scardapane, Simone, et al. "Complex-Valued Neural Networks With Nonparametric Activation Functions." IEEE Transactions on Emerging Topics in Computational Intelligence (2018).
Tsuzuki, Hirofumi, et al. "An approach for sound source localization by complex-valued neural network." IEICE Transactions on Information and Systems 96.10 (2013): 2257-2265.
Virtue, Patrick, X. Yu Stella, and Michael Lustig. "Better than real: Complex-valued neural nets for MRI fingerprinting." 2017 IEEE International Conference on Image Processing (ICIP). IEEE, 2017.

* cited by examiner

COMPLEX-VALUED NEURAL NETWORK WITH LEARNABLE NON-LINEARITIES IN MEDICAL IMAGING

RELATED APPLICATIONS

The present patent document claims the benefit of the filing date under 35 U.S.C. § 119(e) of Provisional U.S. Patent Application Ser. No. 62/713,135, filed Aug. 1, 2018, which is hereby incorporated by reference.

BACKGROUND

The present embodiments relate to machine learning in a complex value domain. Machine learning, such as deep learning using neural networks, is used for image processing and analysis. While most natural and medical images are real-valued images, the nature of the magnetic resonance (MR), ultrasound, and other medical imaging signals in general is described in a complex domain. The phase information from the complex value contains information and is widely used in MR applications such as phase sensitive late gadolinium-enhanced (LGE), flow imaging, or MR fingerprinting. Many neural network systems for MR are derived from applications dealing with real-valued images and operate in the real domain, ignoring the information available from complex MR signals.

Some neural networks use complex signals. Complex-valued neural networks have been utilized for audio signal processing and have gained attention for MR. The complex values are split into separate real and imaginary channels, and real-valued non-linearities are separately applied to each split, such as in a complex ReLU (CReLU) network. This split may distort the phase information. For activation functions (non-linearities), most studies try to provide specific behaviors like preserving the phase through the activation, but there is little proof that the behavior preservation fits the data better.

SUMMARY

Systems, methods, and instructions on computer readable media are provided for machine training and application of a trained complex-valued machine learning model. An activation function of the machine learning model, such as a neural network, includes a learnable parameter that is complex or defined in a complex domain with two dimensions, such as real and imaginary or magnitude and phase dimensions. The complex learnable parameter is trained for any of various applications, such as MR fingerprinting, other medical imaging, or non-medical uses.

In a first aspect, a method is provided for application of a complex-valued neural network for a medical imaging system. An internal region of a patient is scanned by the medical imaging system. The complex-valued neural network is applied to scan data from the scanning and representing the internal region of the patient. The complex-valued neural network includes one or more learned, complex-valued activation functions. An image having an indication output by the complex-valued neural network from the applying is displayed.

In one embodiment, a magnetic resonance scanner scans. The scan data is input as complex values to the complex-valued neural network. The displayed image is a magnetic resonance image. For example, the complex-valued neural network was trained for outputting values of multiple parameters for magnetic resonance fingerprinting, and the displayed image is for one of the parameters where another image is displayed for another of the parameters. The network may have been trained for other phase-sensitive applications, such as MR flow, Dixon, or processing in k-space.

Optionally, the learned, complex-valued activation functions may each include a learned parameter for a relationship between real and imaginary components or between magnitude and phase components. The learned, complex-valued activation functions may be learned non-linearities in a complex-value domain.

In some embodiments, the leaned, complex-valued activation functions each include a machine-learned parameter in a two-dimensional complex grid. For example, the machine-learned parameter is a machine-learned angle as a bias term for rotation in phase of a Cardioid function. As another example, the leaned, complex-valued activation functions include a ReLU with a learned rotation. As yet another example, the machine-learned parameter is a machine-learned mixing coefficient with shifts in the two-dimensional complex grid, a machine-learned kernel with two-dimensional vectors in the two-dimensional complex grid, or both in a kernel activation function. The kernel activation function may be a bivariate kernel activation function. In yet another example, the machine-learned parameter is a machine-learned parameter including a separable kernel of a kernel activation function, where the separable kernel has a polar representation for complex numbers.

The complex-valued neural network being applied may be a fully connected, dropout, batch-normalization, multi-dimensional convolution, average pooling, magnitude-max pooling, magnitude transformation neural network, or any other neural network architecture.

In a second aspect, a medical imaging system is provided for operating on complex-valued data. A medical scanner is configured to scan a patient and generate the complex-valued data from the scan. An image processor is configured to apply the complex-valued data to a machine-learned model. The machine-learned model includes a two-dimensional activation function with two dimensions being real and imaginary or magnitude and phase. At least one learned parameter of the two-dimensional activation function was trained to relate between the two dimensions. A display is configured to display a medical image from an output of the application.

In one embodiment, the two-dimensional activation function is a Cardioid activation function. The learned parameter is a rotation in the two dimensions. In another embodiment, the two-dimensional activation function is a kernel activation function. The learned parameter is a mixing coefficient in both of the two dimensions, a kernel in the two dimensions, or both. In yet another embodiment, the two-dimensional activation function is a kernel activation function. The learned parameter is a separable kernel in a polar representation.

In a third aspect, a method is provided for machine training in a complex-valued neural network. The complex-valued neural network is defined with a Cardioid or kernel activation function. The Cardioid or kernel activation function has a learnable parameter in a real and imaginary or magnitude and phase grid. A machine trains the complex-valued neural network, including training the learnable parameter. The neural network as trained is stored.

Where the activation function is the Cardioid activation function, the learnable parameter may be a rotation in the grid. Where activation function is the kernel activation function, the learnable parameter may be grid shifts in both directions of the grid, variance in both the directions, or both.

Any one or more of the aspects described above may be used alone or in combination. Features, options, or embodiments for one type of aspect (e.g., method) may be used in other types of aspects (e.g., instructions on a non-transitory medium or system). These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF EMBODIMENTS

Complex-valued neural networks include trainable activation functions for magnetic resonance imaging, such MR fingerprinting. Deep learning is provided for MR data with complex-valued data. Other machine-learning models may be used. Other MR, medical imaging, or non-medical imaging applications may be used, such as learning to perform fast Fourier transform or other phase-sensitive MR applications (e.g., flow, Dixon, or processing in k-space). The complex-valued neural network may be trained for and used in other applications.

Different trainable complex-valued activation functions are provided, along with complex-valued linear operations. The complex-valued activation functions are trained, such as training for MR fingerprinting regression. The non-linearities are extended for complex values either by adapting them from the real domain to the complex domain or by adding customizable parameters in their definition. Learnable parameters are included in the definition of the non-linearities. "Learning," "learned," or "learnable" terms refer to the process of backpropagation used to train the neural networks or another machine-learned network. The shape of the different non-linearities for each layer or neuron is learned from the complex-value data.

Separable real activation functions are less expressive once in the two-dimensional (2D) complex domain. 2D activation functions with trainable parameters in a complex-value neural network provide improvement over non-trainable versions. The complex domain grid shift, rotation in complex value space, and/or variance across the complex domain grid may be learned in the complex representation of the activation function. The grid in the complex value domain and/or the covariance may or may not be used as learnable parameters. Complex kernel non-linearities provide a parameterization to learn the shape of the activation function. These learnable parameters for complex values may be learned and bring benefits by using more information in the input complex values. Complex non-linearities (activation function) are designed to fully exploit complex-valued information. The learned non-linearities may maintain the important phase information in the data.

Figure 1:
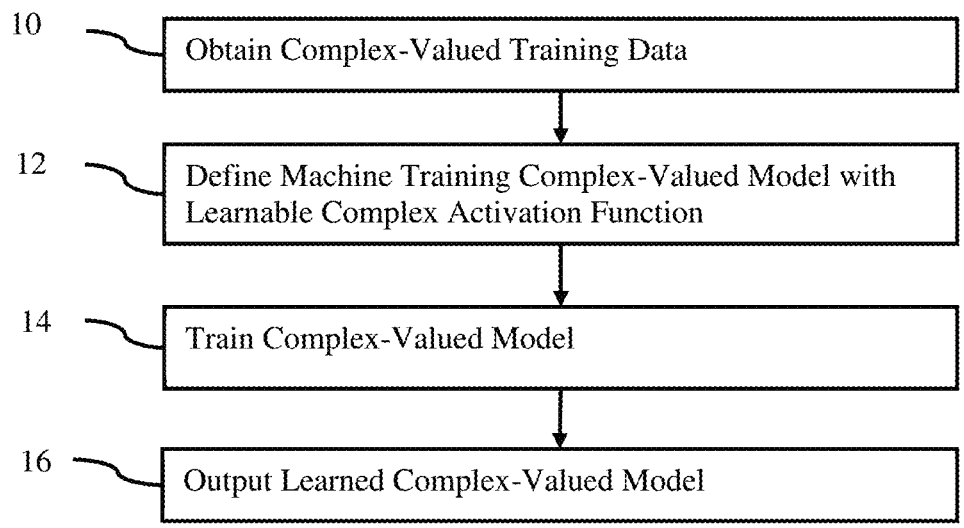
FIG. 1 is a flow chart diagram of one embodiment of a method for machine training a complex-valued model with a learnable complex activation function.
Figure 8:
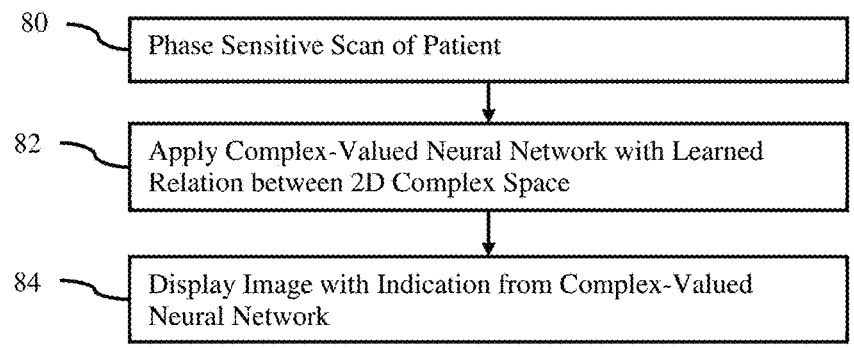
FIG. 8 is a flow chart diagram of one embodiment of a method for application of a complex-value neural network.

FIGS. 1 and 8 show methods related to complex-valued machine modeling. The method may be a method to machine learn or train a complex-valued model or may be a method for application of a machine-learned complex-valued model. FIG. 1 is directed to machine training of the model. FIG. 8 is directed to application of the machine-learned model, such as a complex-valued neural network.

In both cases, a machine, such as an image processor of a medical imaging system, workstation, computer, or server, implements some or all the acts. The same or different machine is used for training and application. The system of FIG. 12 implements one or both methods in one embodiment, but other systems may be used.

A user may select the image files for application of the learned model by the processor or select the images from which to train the model by a processor. Use of the machine allows processing large volumes (e.g., images of many pixels and/or many images) of information that may not be efficiently handled by humans, may be unrealistically handled by humans in the needed time frame, or may not even be possible by humans due to unknown relationships and/or timing. The machine may learn in a way different than a human, improving or diversifying information used for diagnosis, treatment or other purposes. The machine learning provides for the machine to operate more efficiently to assist in imaging or other application in a way different than done by humans.

The methods are provided in the orders shown (e.g., top to bottom or numerical), but other orders may be provided. For FIG. 1, acts 10 and 12 may be performed in a reverse order.

Additional, different or fewer acts may be provided. For example, act 16 of FIG. 1 is not provided. As another example, acts for capturing images, configuring systems, and/or acts using output information are provided.

FIG. 1 shows a method for machine training a complex-valued model. The complex-valued model operates on, receives, outputs, and/or otherwise learns to handle complex signals, such as real and imaginary or magnitude and phase signals. Machine learning learns to relate the input data to an output where at least part of the relation in the model operates in the complex value domain rather than just the real value domain. One or more learnable parameters are in the complex domain rather than learning only real-valued parameters.

In act 20, training data is obtained. The training data is directed to the purpose of the machine training. For example, the machine is to learn a model to relate input MR values to multiple MR parameters in MR fingerprinting. MR data in the image domain (i.e., after transform from k-space) is to be input to the model, and the model outputs values for two or more parameters. In the examples below, the machine is to train a model for MR fingerprinting to output T1 and T2 values, but additional and/or different MR parameters may be used. In other embodiments, the model is trained for other types of MR imaging. MR is naturally complex-valued. The phase information may contain important information, such as in Dixon, phase-sensitive inversion recovery, MR fingerprinting, or MR spectroscopy. The output may be a phase image, such as flow encoding, MR elastography, MR temperature mapping, partial Fourier, off-resonance correction, k-space processing, or other phase-sensitive processing. Alternatively, the model is trained for ultrasound or other types of medical imaging. In yet other alternatives, the model is trained for operating on other types of measurements, such as in an electrical power supply system.

The machine is to train the model to receive input data and output information. The output information is of any type. In the MR fingerprinting example, the output information is values of MR parameters. In other MR examples, other types of information are output. Alternatively, the output is a segmentation, classification, identification, tracking, sequence of acts, or other outputs.

The input data may have complex values. Values with real and imaginary or magnitude and phase (e.g., in-phase and quadrature) components may be input. For example, MR measurements in the k-space domain or after transform to the image domain have complex values.

For training, the training data includes many samples of both the input and the output. For MR fingerprinting, MR measurements based on one or more varying pulse sequences are provided as the input data. Measurements of a same type of object (e.g., heart) are obtained. The measurements are obtained by data transfer, capture, and/or loading from memory. Any number of sample sets of measurements of a same type of object is obtained, such as tens, hundreds, or thousands. The MR measurements are obtained with a same type of scanner, whether being from a same scanner or different scanners of the same type (e.g., using an MR scanner or scanners). The object as occurring in many different patients is included in the collection of MR measurements.

MR scanners capture the MR measurements with gradient coils, a whole-body coil, and/or local coils to transmit a pulse sequence in a magnetic field created by a main magnet or coil. The whole-body coil or local coils receive signals responsive to the re-orientation of molecules shifted due to the pulse sequence.

The MR measurements are used for training in act 14. The MR measurements may be used as received or may be pre-processed, such as segmented, filtered (e.g., noise removal), masked (e.g., removing background information), and/or having geometric features identified (e.g., boundaries, centerlines, and/or hydraulic diameters). In one embodiment of pre-processing, the received images are normalized. Since different settings, imaging systems, patients being scanned, and/or other variations in acquiring MR measurements may result in different offsets and/or dynamic ranges, normalization may result in more uniform representation of the object. Any normalization may be used, such as setting a maximum value to 1 with all other values linearly scaled between 0 and 1. Each volumetric scan or medical image is individually normalized.

The training data includes ground truth samples. In the MR fingerprinting example, the ground truth are MR parameter maps, such as T1 and T2 images. The images may be display values, such as color (e.g., RGB) values, or may be scalar values that may be mapped to display values. For each set of MR measurements, the corresponding parameter maps are provided as ground truth. The training data includes input samples for each of the output (ground truth) samples. Other input information, such as demographics (e.g., group membership), patient information (e.g., history, age, sex, weight, body-mass-index, body surface area, heart pressure, and/or heart rate), blood biomarkers, and/or genetic information, may be provided as input of the samples. For semi-supervised or unsupervised learning, the training data may not include ground truth samples.

In act 12, a machine learning model or architecture is defined. The definition is by configuration or programming of the learning. The number of layers or units, type of learning, and other characteristics of the model are controlled by the programmer or user. In other embodiments, one or more aspects (e.g., number of nodes, number of layers or units, or type of learning) are defined and selected by the machine during the learning.

The machine learning model is a support vector machine, k-means cluster, Bayesian network, or other type of machine learning and corresponding architecture. In one embodiment, the model and corresponding architecture is a neural network for deep learning. Deep architectures or neural networks include convolutional neural network (CNN) or deep belief nets (DBN), but other deep networks may be used. CNN learns feed-forward mapping functions while DBN learns a generative model of data. In addition, CNN uses shared weights for all local regions while DBN is a fully connected network. The training of CNN is entirely discriminative through back-propagation. DBN, on the other hand, employs the layer-wise unsupervised training (e.g., pre-training) followed by the discriminative refinement with back-propagation if necessary Any neural network architecture may be used, such as a convolutional, fully connected convolutional, dense, image-to-image, U-net, convolutional-to-transposed-convolutional, generative, generative adversarial, or other architecture. The architecture includes one or more of any types of layers, such as fully connected, dropout, batch-normalization, multi-dimensional convolution, average pooling, magnitude-max pooling, magnitude transformations, activation, or other layers. The network is defined as a plurality of sequential feature units or layers. Sequential is used to indicate the general flow of output feature values from one layer to input to a next layer. The information from the next layer is fed to a next layer, and so on until the final output. The layers may only feed forward or may be bi-directional, including some feedback to a previous layer. Skip connections may be used. The nodes of each layer or unit may connect with all or only a sub-set of nodes of a previous or subsequent layer or unit.

Within a unit or layer, any number of nodes is provided. For example, 100 nodes are provided. Later or subsequent units or layers may have more, fewer, or the same number of nodes. The features of the nodes are learned by the machine using any building blocks. For example, autoencoder (AE) or restricted Boltzmann machine (RBM) approaches are used. AE transforms data linearly, and then applies a non-linear rectification, like a sigmoid function. The objective function of AE is the expected mean square error between the input image and reconstructed images using the learned features. AE may be trained using stochastic gradient descent or other approach to learn, by the machine, the features leading to the best reconstruction. The objective function of RBM is an energy function. Exact computation of the likelihood term associated with RBM is intractable. Therefore, an approximate algorithm, such as contrastive-divergence based on k-step Gibb sampling or other, is used to train the RBM to reconstruct the image from features.

Training of AE or RBM is prone to over-fitting for high-dimensional input data. Sparsity or denoising techniques (e.g., sparse denoising AE (SDAE)) are employed to constrain the freedom of parameters and force learning of interesting structures within the data. Enforcing sparsity within hidden layers (i.e., only a small number of units in hidden layers are activated at one time) may also regularize the network. In other embodiments, at least one unit is a convolution with ReLU activation or is a batch normalization with a ReLU activation followed by a convolution layer (BN+LeakyRU+convolution). Different units may be of the same or different type. Cardioid, kernel, or other types of activations functions may be used.

Figure 2:
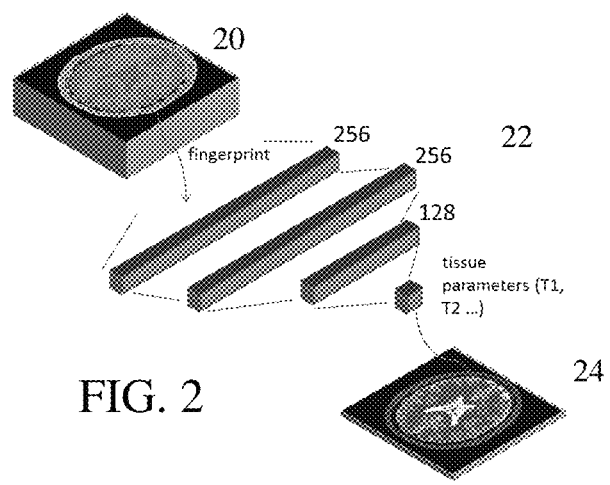
FIG. 2 illustrates an example neural network for MR fingerprinting.

FIG. 2 shows one example neural network as the defined architecture. Three fully connected layers are provided in sequence. The fully connected layers include 256, 256, and 128 neurons or nodes, respectively. Other numbers of layers, arrangement or order of layers, numbers of nodes, or architectures may be used.

Each or some of the nodes are defined with an activation function. The same or different activation functions are provided for the different nodes. One or more variables or parameters of the activation functions are learnable. The machine training of act 14 learns the value or values of the parameter or parameters to relate the input to the function to the output. For operation in the complex value domain, the activation function defines a complex non-linearity. The activation function for one or more nodes, such as all the nodes with activation functions, are implemented in the complex-value domain. The model for machine learning is defined to include one or more learnable complex-valued activation functions. The complex-valued activation functions each include one or plural learnable parameters for a relationship between real and imaginary components or between magnitude and phase components. By defining the activation function in a two-dimensional complex value domain, the relationship between the two components of the signal may be learned.

In the MR fingerprinting example used herein, a complex-valued neural network is defined to include activation functions with one or more learnable complex parameters or parameters defined in both real and imaginary or both magnitude and phase components. The learnable parameter is in a two-dimensional complex grid.

Any activation function may be used. For example, the complex-valued neural network is defined to include a Cardioid or kernel activation function. The Cardioid is altered to include a learnable parameter. The modified Cardioid function or kernel activation function has a learnable parameter in a real and imaginary or magnitude and phase grid. Other activation functions may be used.

For the Cardioid activation function, the learnable parameters are a rotation in the grid. The rotation of the activation function in the complex value space relates the two components (e.g., x-axis real component to the y-axis imaginary component). The rotation is an angle to be machine learned as a bias term for rotation in phase of the Cardioid function. A ReLU activation function may include a learned rotation in the complex value space.

The Cardioid function is: $f(z)=\frac{1}{2}(1+\cos(\angle z))z$, where $z$ is the input value. The Cardioid function may be considered as a smoother version of a complex ReLU (CReLU), where the real and imaginary parts are separately handled as real values. This Cardioid function has a fixed orientation toward the real axis. To include a complex parameter, the trainable Cardioid function may orient differently in the 2D complex plane for each neuron by introducing a bias term in the phase as: $f(z)=\frac{1}{2}(1+\cos(\angle z+\angle b))z$ where $\angle b$ is the rotation learned through training. The behavior concerning the phase of the complex numbers as input is to be learned where the magnitude is modulated according to a specific angle. The Cardioid function with the learnable rotation in the complex plane may be expressed in other ways, such as:

$$f(z) = \frac{1}{2}\left(1 + \frac{z_r b_r - z_i b_i}{|z||b|}\right)z.$$

Other expressions may be used. Other activation functions with a learnable rotation in the complex plane (2D grid) may be used.

The learnable parameter for the relationship between complex components may be separately learned for each activation function or node. The orientation or rotation in the 2D complex plane or grid may be different for each node. Alternatively, the learnable parameter is constrained to be the same for all or a sub-set of the activation functions or nodes.

For the kernel activation function, the learnable parameter may be grid shifts in both directions of the 2D complex value grid, may be variance in both the directions, or both. The grid shifts may be part of a learnable mixing coefficient. The variance may be part of a learnable kernel with 2D vectors in the 2D complex grid. The kernel activation function with the learnable parameter or parameters in the 2D complex grid may be a bivariate kernel activation function.

The kernel activation function may be represented as: $f(z)=\sum_{n=1}^{D}\alpha_n K(z, d_n)$, where K is the Gaussian kernel defined as $K(z, d)=e^{-\gamma(z-d)^2}$, where D is the number of kernels (e.g., 20), $\alpha_i$ are the trainable mixing coefficients, and $d_i$ are the positions of the kernels evenly distributed on a 1D grid. For the bivariate real Gaussian kernel, the 2D grid of mixing coefficient is represented by: $f(z)=\sum_{n=1}^{D_1}\sum_{m=1}^{D_2}\alpha_{n,m}K(z, d_n+id_m)$, where n and m are indexes for the 2D complex grid. The shifts are over the complex plane. The kernel may be designed for complex numbers as 2D vectors, represented as $K(z, d)=e^{-(z-d)^T\Theta^{-1}(z-d)}$ where $\Sigma$ is the kernel covariance or covariance matrix.

In general, one or more parameters are defined for learning non-linearities. For a Gaussian kernel, the (co)variance terms (γ/Σ) allow changing the distribution of each Gaussian window. The grid shifts (d) allow learning the grid repartition of the mixed window functions. Z and d are both complex numbers represented as 2D vectors in the complex plane or 2D grid. The mixing coefficients α may be real or complex numbers. If real numbers are used, then the function is multiplied by $e^{i\angle z}$ to conserve phase information. Other window functions may be used. Rather than learn α coefficients only as real values for modulating any grid of specific window functions, such as the Gaussian window function, the activation function is extended to learning the shifts or variance relating the complex components to each other. The activation function includes one or more learnable parameters with a high prior on how the function can shape, such as the covariance for the bivariate Gaussian window.

In this approach for the kernel activation function, the 2D grid is a Cartesian grid (e.g., real/imaginary). The complex equivalent of the real kernel activation function is applied using a bivariate real Gaussian window function. The covariance matrix is the 2D equivalent of the variance coefficient and may be learned. In another approach for the kernel activation function, a polar 2D grid (e.g., magnitude and phase) is used for the complex values. The learnable parameter is a separable kernel where the separable kernel has a polar representation for complex numbers. The polar representation describes the complex number. In one embodiment, the kernel activation function with the 2D grid described in polar coordinates is represented as: $f(z)=\sum_{n=1}^{D_1}\alpha_n K(|z|,d_n)e^{ig_n(z)}$ where $g_n(z)=\sum_{m=1}^{D_2}\alpha_{n,m}K(\angle z, d_{n,m})$, where $d_n$ represents the shifts over a 1D magnitude grid, and $d_{m,p}$ represents the shifts over a 2D magnitude and phase grid. K is a real function. The activation function includes one or more learnable parameters with a high prior on how the function can shape, such as the parameters to manipulate the shape using explicitly the magnitude and phase instead or real and imaginary parts.

Other activation functions with one or more learnable parameters relating complex components together or defined in the complex value domain (e.g., on the complex 2D grid or plane) may be used. The same function is provided in any number of nodes, which are separately defined to learn corresponding values for the parameters. Alternatively or additionally, different functions may be used in different nodes.

In act 14 of FIG. 1, a machine (e.g., image processor, workstation, computer, or server) trains the model (e.g., complex-valued neural network) with the training data having ground truth. In the MR fingerprinting example, the neural network is trained using the MR measurements with complex values and the ground truth T1 and T2 parameter maps. Machine learning is performed to train the various layers and nodes using the defined architecture. The values of the learnable parameters of the activation functions are learned, including the parameters defined in the complex domain. Values of other parameters, such as connections, weights, or other real-valued parameters are learned. The values of the learnable parameters providing the desired result given inputs are learned. The training may learn the relationship of other data, such as demographics, patient information, blood biomarkers, and/or genetic information, to the output.

The results relative to the ground truth and the error for reconstruction for the network are back-projected to learn the values for the learnable parameters that work best. In one embodiment, a L2-norm loss is used to optimize the network. Other error functions may be used. End-to-end training is performed, but one or more features may be set. Batch normalization, dropout, and data augmentation are not used, but may be. The optimization is with the Adam optimizer, but other optimization functions (e.g., RMSprop, SGD, etc.) may be used. During the optimization, the different distinguishing values of learnable parameters are learned, such as learning the angle for a Cardioid activation function of a given node and/or the shifts or variance for a kernel activation function of a given node.

The network learns to output in response to input. For example, the network learns to output T1 and T2 parameter maps or images based on input MR measurements from an MR fingerprinting scan. The output is for spatially distributed locations, such as outputting T1 and T2 values for real 2D or 3D locations based on MR measurements for the same or different locations. The output is not spatial in other embodiments, such as outputting a classification. Once trained, the model may be applied to generate the output from new inputs.

The many samples in the training data are used to learn. The machine learning model is trained to learn the correspondence between the input and the output where one or both of the input or output have complex values. The complex-valued neural network or other model is machine trained by the machine. For example, the complex-valued neural network is trained to regress complex-valued fingerprints (MR measurements) to real-valued tissue parameters (e.g., T1, T2).

For comparison of performance, the neural network of FIG. 2 (i.e., three hidden fully-connected layers of 256, 256 and 128 neurons, respectively) is trained to form different complex-valued neural networks using different activation functions. The same activation function is used in each of the nodes of the three fully connected layers for each of the complex-valued neural networks. Real-valued neural networks with ReLU and kernel activation function and complex-valued neural networks with separable components (i.e., CReLU and Cardioid) and related components (i.e., rotated Cardioid, bivariate kernel activation function and polar kernel activation function) are tested. For CReLU and Cardioid without the learned rotation in the complex value domain, the complex-valued data is split into real and imaginary components and applied as real-valued non-linearities separately to each split. This approach may alter the phase information and is not ideal for complex data as the relationship between the complex components is not learned. The rotated Cardioid, bivariate kernel, and polar kernel activation functions learn the relationship in the complex plane.

The input data is MR measurements for MR fingerprinting to T1 and T2 parameter maps as the ground truth. Using deep learning, the deep neural networks are trained to regress temporal complex-valued MRF signal to a vector of tissue parameters. 100 k TrueFISP fingerprint signals with random initial phases are used for training (90%) and validation (10%) with a wide range of T1s and T2s. Brainweb data is used for testing. Training uses $L_2$ loss and the Adam algorithm. For the KAFs, the number of kernels was determined empirically as a grid of 20 elements for the real activation, a grid of 10 by 10 for the bivariate kernel, and finally a magnitude grid of 20 by 1 and a phase grid of 20 by 1 for the polar kernel.

Figure 3:
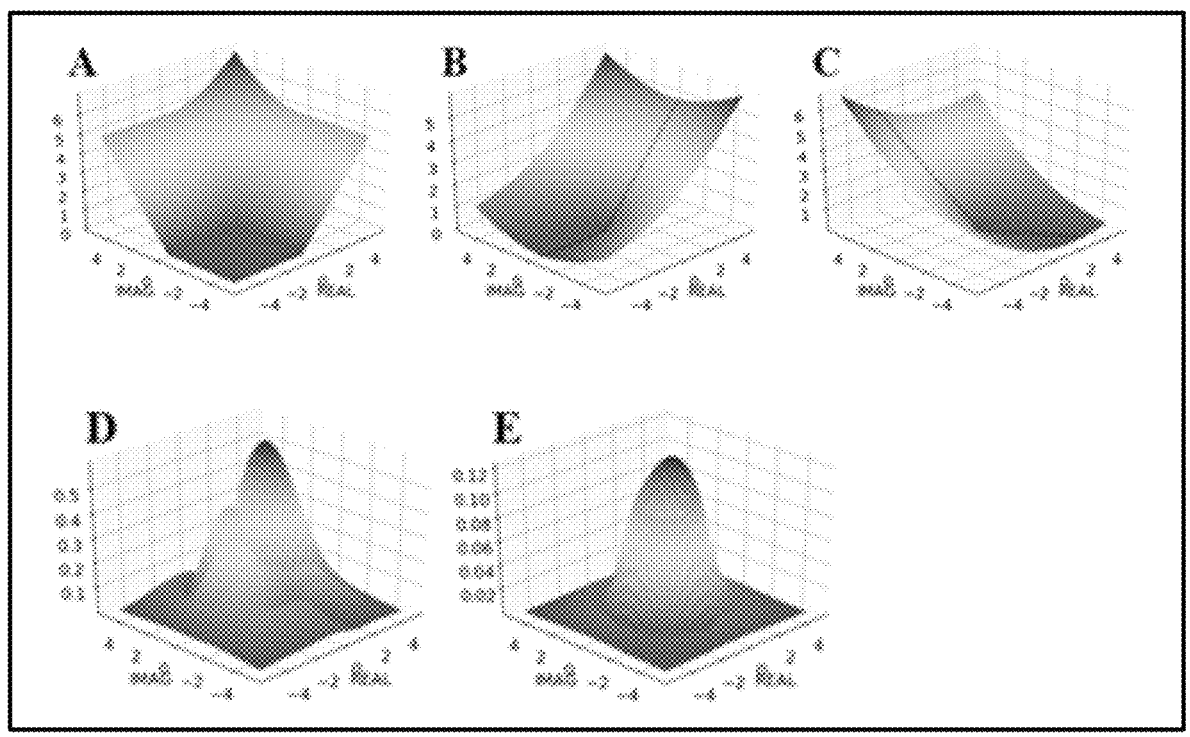
FIG. 3 illustrates example learned activation functions in two-dimensional complex space.

To compare the trained results, root mean square error (RMSE) and relative error percentage (err %) are measured as compared to the ground truth. FIG. 3 shows some example learned activation functions of: A-CReLU, B-Cardioid, C-Rotated Cardioid, D-Bivariate KAF, and E-Polar KAF. For the rotated Cardioid, the rotation in the complex plane is reflected by the change in angle of the dashed line as compared to the Cardioid activation function without the learned angle (i.e., B).

Figure 4:
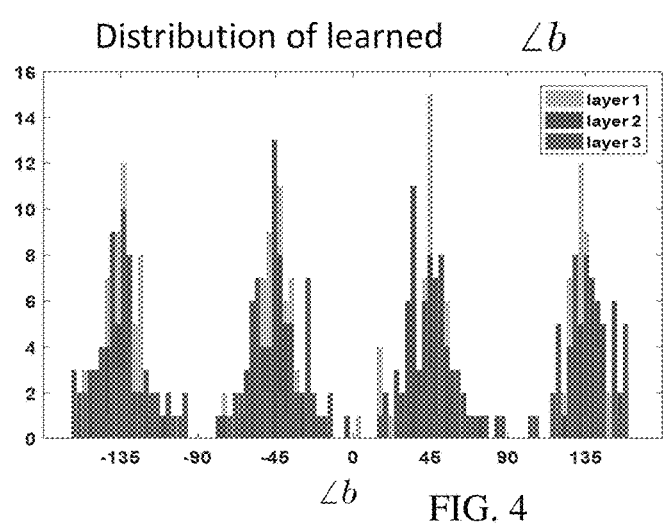
FIG. 4 illustrates histograms of learned rotation biases of three layers in a Cardioid activation function.
Figure 5:
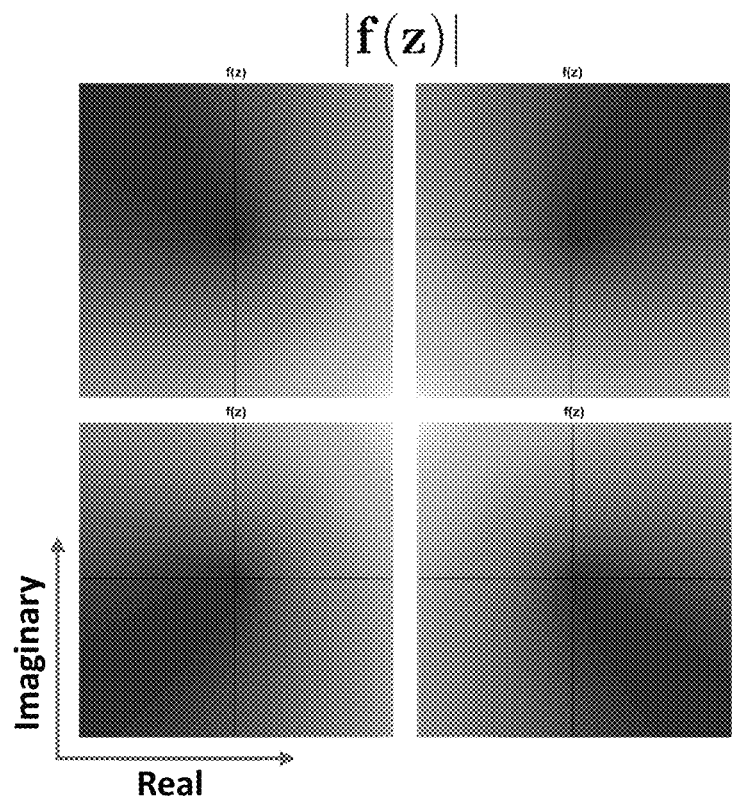
FIG. 5 illustrates four example learned activation functions in a complex-value domain for a Cardioid activation function.
Figure 6A:
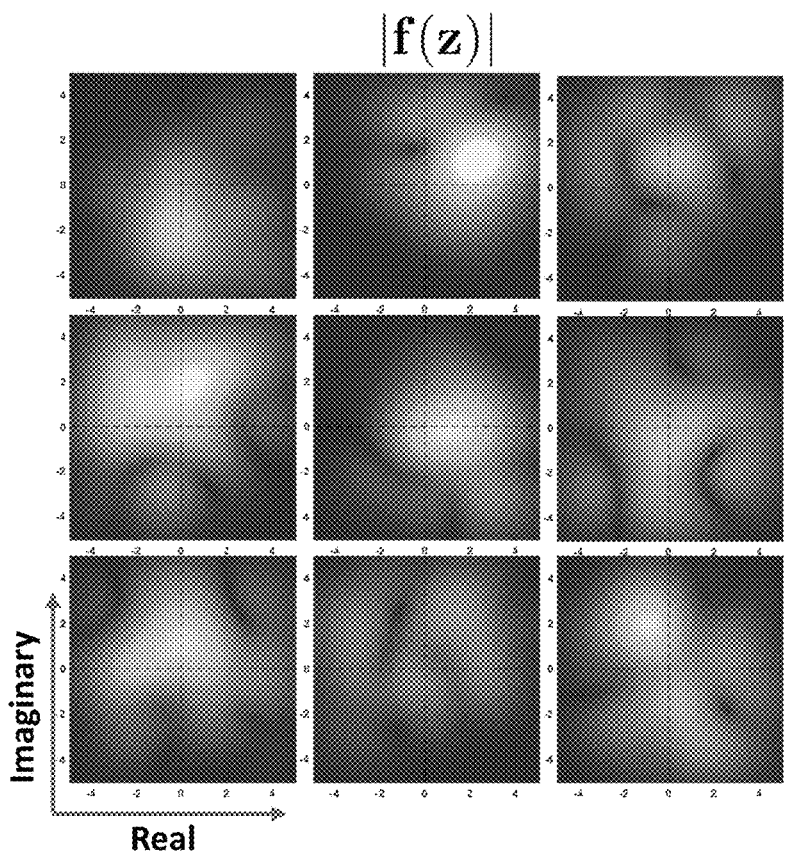
FIGS. 6A and 6B illustrate nine example learned activation functions in a complex-value domain for a bivariate kernel activation function.
Figure 6B:
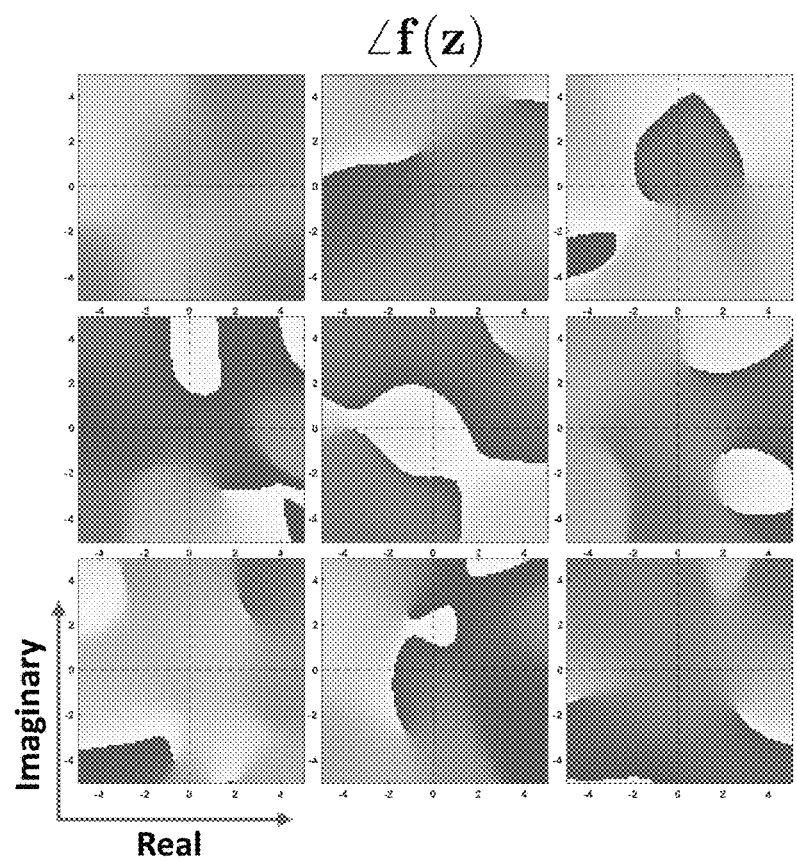
Figure 7A:
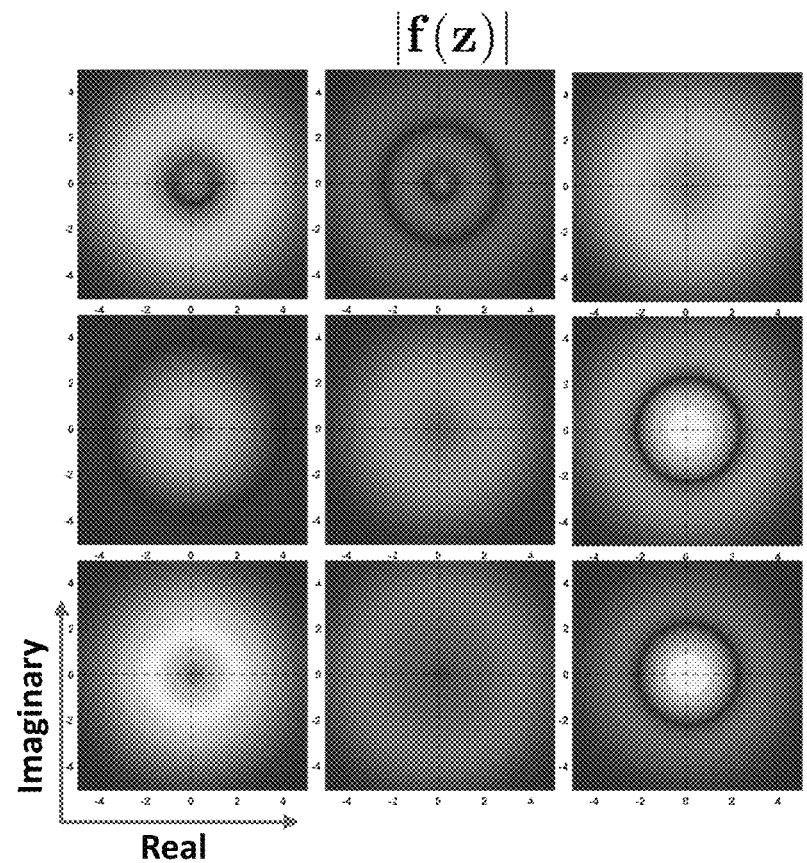
FIGS. 7A and 7B illustrate nine example learned activation functions in a complex-value domain for a polar kernel activation function.
Figure 7B:
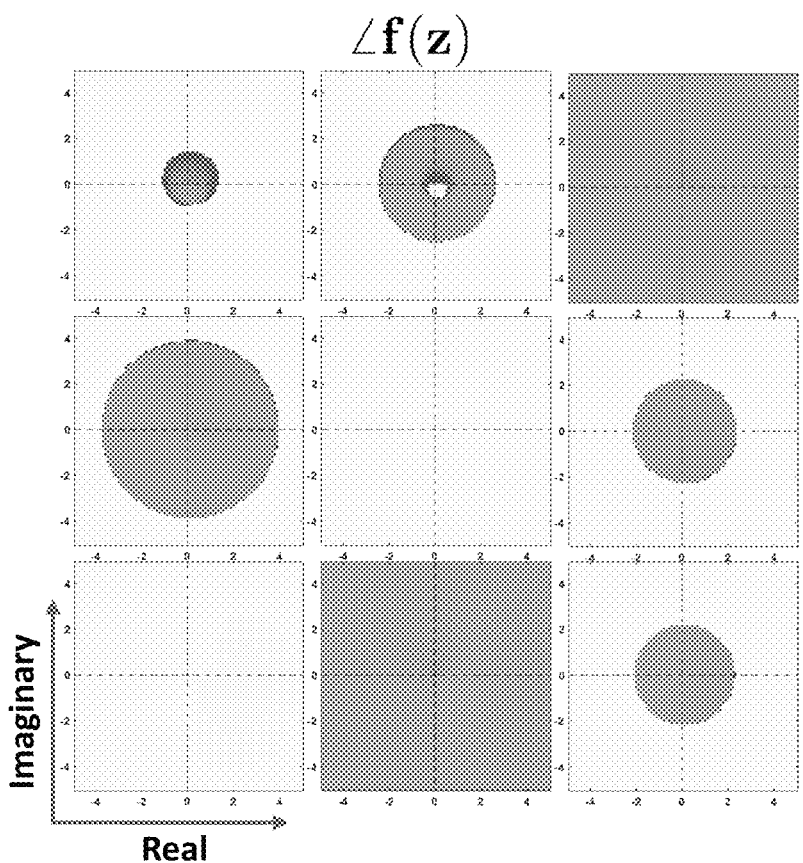

FIG. 4 shows three histograms of the distribution of the learned angles across the nodes of each layer for the complex-valued neural network using the rotated Cardioid. FIG. 5 shows four example activation functions in the complex plane for the complex-valued neural network using the rotated Cardioid. FIGS. 6A, 6B, 7A, and 7B each show nine example activation functions in the complex plane for the complex-valued neural network using the bivariate kernel activation function and the complex-valued neural network using the polar kernel activation function, respectively. These example functions show the alteration to both magnitude and phase (or real and imaginary).

In act 16, the machine outputs a trained network. The machine-learned network is network incorporating the deep learned features for the various units and/or layers of the network and/or the relationships of input features to the output. Once trained, a matrix, kernels, or other trained network is output. The data represents the trained architecture. The machine-learned network includes definitions of convolution kernels, links, weights, pooling, and/or other characteristics of the network as trained, including activation functions and the learned parameters.

The machine-learned model is output to a network or memory. For example, the neural network as trained is stored in a memory for transfer and/or later application.

The machine-learned network may estimate the output from an input. Once the network is trained, the network may be applied. The network with defined or learned features is used to extract from previously unseen input measurements with or without other inputs (e.g., patient information). The machine-learned network uses extracted features from the input with or without other information to estimate the output.

The RMSE and err % of the Brainweb test with different activation functions are summarized in Table 1, where KAF is the kernel activation function. KAF methods performed better than the others and polar KAF achieved the best scores. All complex-valued neural networks with trainable activation functions (i.e., Rotated Cardioid, Bivariate KAF, and Polar KAF) outperformed their counterparts (i.e., ReLU, CReLU, Cardioid, and KAF) with fixed activation functions, at least fixed with respect to the relationship between the complex components.

| ACTIVATION | T1 (ms) | T2 (ms) | T1 (%) | T2 (%) |
|---|---|---|---|---|
| ReLU | 18.94 | 6.40 | 1.99 | 3.87 |
| CReLU | 14.92 | 5.98 | 1.29 | 3.93 |
| Cardioid | 11.68 | 12.47 | 0.94 | 3.74 |
| Rotated Cardioid | 8.55 | 5.58 | 0.48 | 2.92 |
| KAF | 8.15 | 4.55 | 0.37 | 3.44 |
| Bivariate KAF | 9.00 | 3.65 | 1.01 | 1.95 |
| Polar KAF | 4.25 | 3.71 | 0.35 | 1.44 |

The RMSE (ms) of the complex-valued neural network of FIG. 2 with polar KAFs is the smallest for T1. The error % is the smallest for both T1 and T2. The RMSE of the bivariate KAF for T2 is the smallest. Including the learnable complex parameter or parameter defined in the complex plane or 2D grid to relate between the complex components provides improved performance in parameter mapping as compared to using real-valued data only in the activation function, even where the phase or imaginary component is included as a real value.

FIG. 8 is a flow chart diagram of one embodiment for application of a complex-valued neural network. In one example, the application is for a medical imaging system, such as an MR scanner. In other examples, the application is for other sensors or devices with complex value data or output. The complex-valued neural network or other machine-learned model receives as input, operates on, and/or outputs complex-valued data. For operating in the complex value domain, the neural network includes one or more activation functions with one or more learned parameters relating the different components of the complex values together. A learned complex parameter is included as part of the activation function.

Figure 12:
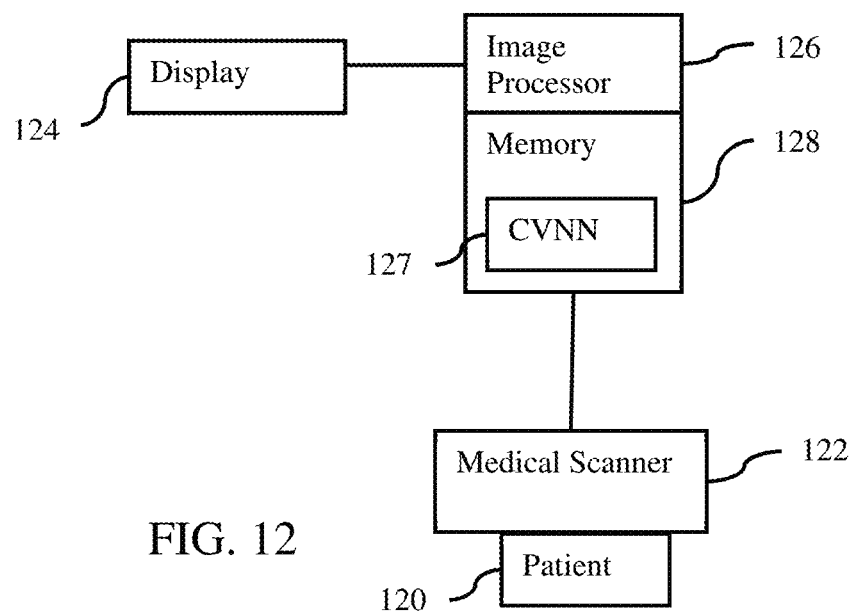
FIG. 12 is a block diagram of one embodiment of a system for operating on complex-valued data.

The same image processor or a different image processor than used for training applies the learned complex parameters of the activation functions and/or complex-valued neural network. For example, the network architecture, learned weights, and learned activation functions are transmitted from a graphics processing unit or artificial intelligence processor used to train to a medical scanner, medical server, or medical workstation. An image processor of the medical device applies the machine-learned network. For example, the medical imaging system of FIG. 12 is used. In one embodiment, the medical scanner or a work station at a same facility as the medical scanner applies the machine-learned network. In another embodiment, a server remote from the medical scanner and/or remote from a facility with the medical scanner applies the machine-learned network, such as providing image processing as a service based on input from a client.

In act 80, a medical imaging system scans an internal region of a patient. For example, a magnetic resonance scanner scans the patient, such as with a pulse sequence for fingerprinting. The image processor receives MR measurements. The MR measurements are from a scan of a patient and include phase-sensitive signal (i.e., are complex signals). Other phase-sensitive scanning may be performed, such as for MR flow, Dixon, or k-space processing. Other types of medical imaging systems, such as ultrasound, may be used. Other non-medical systems may be used to acquire phase sensitive data.

The resulting scan data is received from or by the MR system. The receipt is by scanning the patient. Alternatively, the receipt is by receiving from a network interface. In other embodiments, receipt is by loading from memory.

The MR measurements may be processed, such as reconstructing a plane or volume of the patient from k-space data. Alternatively, the MR measurements are after reconstruction, filtering, or another image processing maintaining the phase information. The received MR measurements may be pre-processed, such as normalized, filtered, noise removed, masked, geometric features identified, and/or segmented in a same way as the training MR measurements. The received MR measurements are to be used to generate the output learned by the complex-valued neural network, such as multiple MR parameter maps.

The type or modality of medical imaging system used for scanning is the same type or modality of medical imaging system used to produce the data for training. The same or different scanner may be used, but the same physics (e.g., x-ray, ultrasound, or magnetic resonance) is used.

In act 82, the image processor applies the complex-valued neural network to the scan data from the scanning and representing the internal region of the patient. The complex-valued data (e.g., MR measurements from a fingerprinting scan) are input to the machine-learned complex-valued model. The complex-valued scan data representing scan response for locations distributed in two or three dimensions within the patient are input to the machine-learned complex-valued neural network, which outputs complex values or real values in response (e.g., outputs T1 and T2 parameter maps of T1 and T2 values representing the locations). The machine-learned complex-valued neural network is applied to the input data to generate the output. Any inputs for which the network is trained to use are applied as an input feature vector, such as pre-processed MR measurements with or without other information (e.g., demographics, patient information, and/or blood biomarkers).

In one embodiment, the machine-learned complex-valued neural network is a fully convolutional network. The learned network may include and apply one or more different types of layers, including fully connected, dropout, batch-normalization, multi-dimensional convolution, average pooling, magnitude-max pooling, or magnitude transformation. By applying the complex-valued neural network, the output is generated. For example, the trained convolution units, weights, links, activation functions, and/or other characteristics of the network are applied to the scan data to extract the corresponding MR parameter maps through a plurality of layers.

By application, the image processor generates the output, such as outputting flow, Dixon, fingerprinting, or k-space processing results based on having been trained for such output. The machine-learned model is used to the output for a previously unseen input (e.g., MR measurements for a patient being diagnosed and/or treated).

The learned non-linearities in complex form are applied as part of the activation functions of the complex-valued neural network. These complex-valued activation functions include the learned value for a complex parameter, such as a parameter relating between the real and imaginary components or between magnitude and phase components of the 2D complex grid. For example, the machine-learned angle as a bias term for rotation in phase of a Cardioid function or a ReLU with a learned rotation may be applied. The rotatable Cardioid activation function or functions are applied. As another example, a machine-learned mixing coefficient with shifts in the two-dimensional complex grid, a machine-learned kernel with two-dimensional vectors in the two-dimensional complex grid, or both are applied in a kernel activation function. A bivariate kernel activation function may be applied. In yet another example, a separable kernel of a kernel activation function where the separable kernel has a polar representation for complex numbers is applied. The polar kernel activation function may be applied.

In act 84, the image processor outputs (e.g., displays or outputs to a computerized medical record) an image having an indication output by the complex-valued neural network from the application. The output of the complex-valued neural network is output as the indication. Alternatively, the output is used to derive the indication, such as outputting a segmentation used to then segment prior to imaging. Any indication may be output, such as an image, classification, segmentation, identification, location determination, diagnosis, prognosis, and/or treatment. The image may be of a report or represent the internal region of the patient with annotation or other content based on the output from the complex-valued neural network.

In one embodiment, the image processor generates an image from the output of the complex-valued neural network. For example, an MR image is generated from the output. In MR fingerprinting, the network outputs two or more parameter maps. The image processor generates a grayscale or color image or images based on the values of the parameter maps, such as generating T1 and T2 images or an image with different pixel characteristics mapped to different ones of the parameters.

Figure 9:
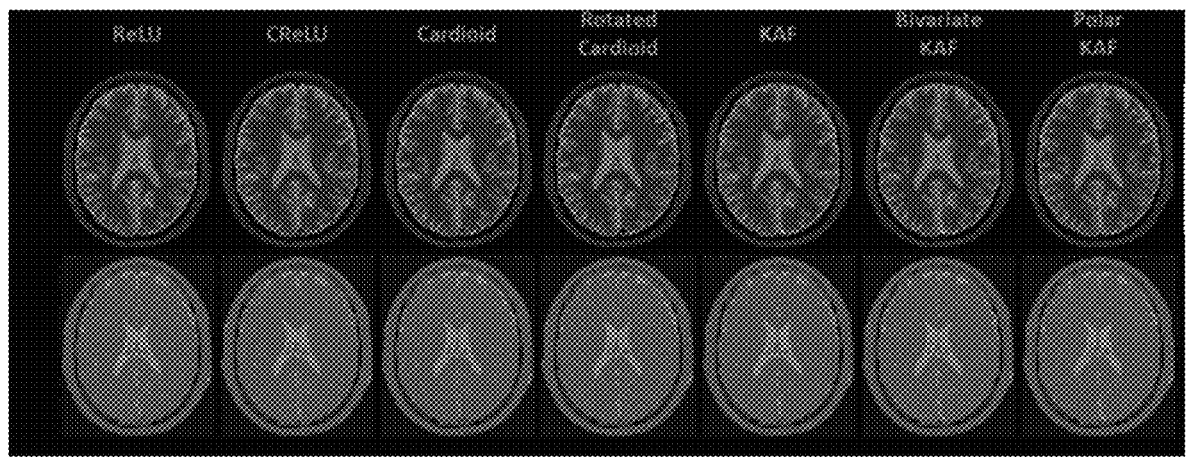
FIG. 9 shows example T1 and T2 maps from application of complex-value neural networks trained with different activation functions.

FIG. 9 shows example outputs. The neural networks trained using the different activation functions are fed the same MR measurements from MR fingerprinting. T1 and T2 parameter maps are output by the complex-valued neural networks, and the parameter maps are mapped to color images (shown in grayscale) where the top row is T1 and the bottom row is T2 for a given slice through the brain of a patient.

Figure 10:
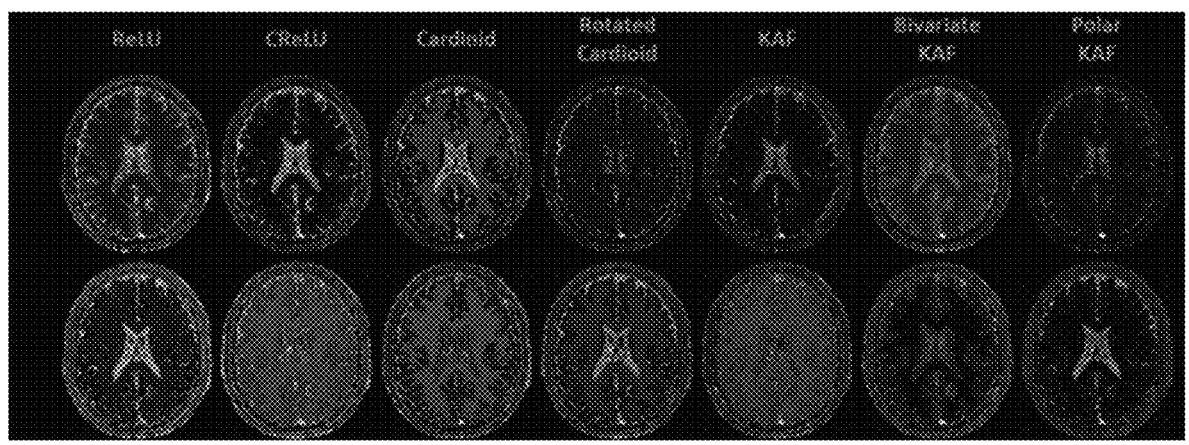
FIG. 10 shows example errors for the T1 and T2 maps of FIG. 9 from a ground truth.

FIG. 10 shows example error maps. The difference between the output T1 and T2 images (see FIG. 9) and the ground truth is mapped to grayscale display values. The darker images represent a lesser difference. The complex-valued neural network using the polar kernel activation functions show the lesser difference from the ground truth. Table 1 above shows the RMSE and error % across a range of test images.

Figure 11:
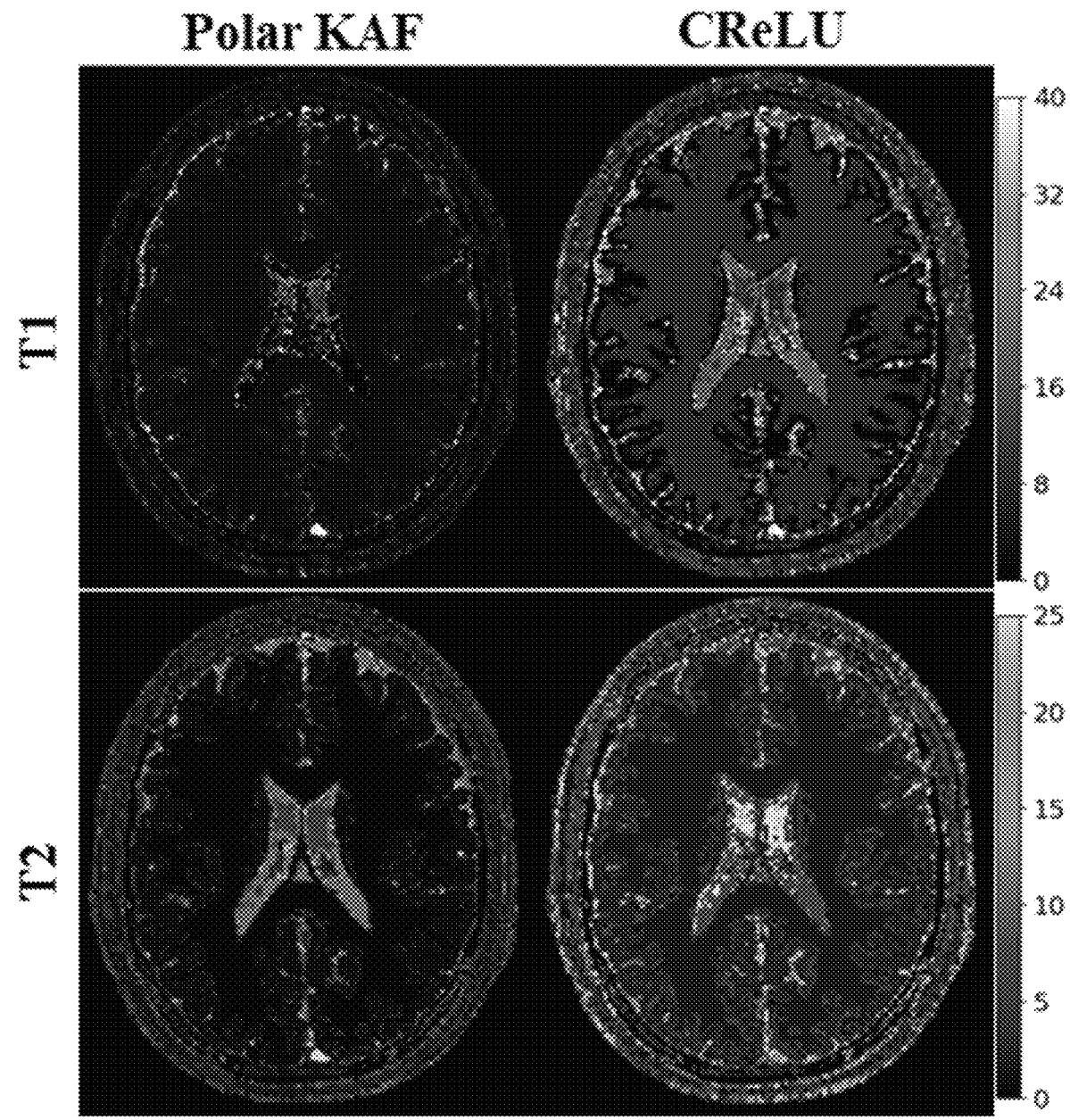
FIG. 11 shows example T1 and T2 error maps from application of a complex-value neural network trained with CReLU (complex values separated into two real values) and with a learned polar kernel activation function.

FIG. 11 shows example error maps (e.g., difference from ground truth) of T1 and T2 estimated from polar KAF and CReLU. The neural network with CReLU activation uses the complex value components separately as real values and provides the most accurate (least difference) of the complex-valued neural networks without a learnable complex parameter. As shown in table 1, polar KAF provides the least different (most accurate) of the complex-valued neural networks with a learnable complex parameter. The polar KAF error map shows less error than the CReLU error map, indicating better performance.

FIG. 12 shows a medical imaging system for operating on complex-valued data, whether as input or generated within the machine-learned model. One or more activation functions include a learnable or learned complex-valued parameter for operating on the complex-valued data.

While shown as a medical imaging system, other embodiments are for a medical treatment or non-medical uses. The medical imaging system includes the display 124, memory 128, and image processor 126. The display 124, image processor 126, and memory 128 may be part of the medical scanner 122, a computer, server, or other system for image processing medical images from a scan of a patient. A workstation or computer without the medical scanner 122 may be used as the medical imaging system. Additional, different, or fewer components may be provided, such as including a computer network for remote generation of output from locally captured scans or for local output from remotely captured scans. The complex-valued neural network 127 is applied as a standalone application on the workstation or a local device or as a service deployed on a computer network (cloud) architecture.

The medical imaging system is for training, such as using MR measurements from the memory 128 and/or medical scanner 122 as input samples and corresponding ground truth. Alternatively, the medical imaging system is for application of the machine-learned network 127.

The medical scanner 122 is a medical diagnostic imaging system configured to scan a plane or volume of a patient and generate anatomical information from the scan. In one embodiment for application of the machine-learned network, the medical scanner 122 is an MR system configured for tissue scanning, such as MR fingerprinting scan. A main magnet or coil generates a substantially uniform magnetic field through the patient 120. Gradient coils, local coils, and/or a whole-body coil generate a pulse sequence to shift spin axes of molecules in the patient away from the uniform magnetic field lines. The local coils and/or whole-body coil detect radio frequency emissions caused by the relaxation of the spin axes of the molecules returning to the magnetic field lines. This k-space data is reconstructed into an object or spatial domain using Fourier processing. The resulting scan data represents tissue response from the region of the patient. Any MR imaging pulse sequence or scanning may be used, such as for Dixon or flow imaging.

In another embodiment, the medical scanner 122 is an ultrasound scanner. Transmit and receive beamformers use an ultrasound transducer to acoustically scan a volume of the patient. The received signals are applied to a detector for tissue response, such as a B-mode detector, or for flow response, such as a Doppler processor.

Other medical scanners generating complex-valued measurements or phase-sensitive outputs may be used. The medical scanner 122 is configured to scan the patient 120 and generate complex-valued data from the scan.

The image processor 126 is a control processor, general processor, digital signal processor, three-dimensional data processor, graphics processing unit, application specific integrated circuit, field programmable gate array, artificial intelligence processor, digital circuit, analog circuit, combinations thereof, or other now known or later developed device for operating on complex-valued data. The image processor 126 is a single device, a plurality of devices, or a network of devices. For more than one device, parallel or sequential division of processing may be used. Different devices making up the image processor 126 may perform different functions, such as applying the machine-learned complex-valued neural network 127 to generate MR parameter maps and a separate device for generating an image based on the MR parameter maps. In one embodiment, the image processor 126 is a control processor or other processor of a medical diagnostic imaging system, such as the medical scanner 122. The image processor 126 operates pursuant to stored instructions, hardware, and/or firmware to perform various acts described herein, such as controlling scanning, applying machine-learned complex-valued neural network or model, and/or generating an output image showing an indication of the output of the network or model.

The image processor 126 is configured to train a machine learning architecture. Based on a user provided or other source of the network architecture and training data, the image processor 126 learns values for learnable parameters relating complex components of activation functions. The result of the training is a machine-learned complex-valued model or neural network.

Alternatively or additionally, the image processor 126 is configured to apply one or more machine-learned complex-valued models or neural networks. Complex-valued data is applied to the machine-learned model, which includes a 2D activation function with the dimensions being real and imaginary or magnitude and phase. At least one learned parameter of the 2D activation function relates between the two dimensions (i.e., relates between complex components, such as a rotation or shift in the complex plane). For example, the 2D activation function is a Cardioid activation function, and the learned parameter is a rotation in the two dimensions. As another example, the 2D activation function is a kernel activation function, and the learned parameter is a mixing coefficient in both of the two dimensions, a kernel in the two dimensions, or both. In yet another example, the 2D activation function is a kernel activation function, and the learned parameter is a separable kernel in a polar representation.

The image processor 126 may be configured to output an image showing information from or responsive to output of the complex-valued machine-learned model or neural network. An image of anatomy based on a map output by the model, an image of a report with a classification or quantification output by the model, or other output is represented in the image. Any of the images may or may not also include anatomical information, such as an MR image of tissue overlaid with output classification information for some spatial locations.

The display 124 is a CRT, LCD, projector, plasma, printer, tablet, smart phone or other now known or later developed display device for displaying the output, such as a MR image or combination of MR images (e.g., T1 and T2 images). The display 124 displays a medical image generated from the output of the application of the complex-valued machine-learned model.

The instructions, medical images, network definition, features, machine-learned network, outputs, and/or other information are stored in a non-transitory computer readable memory, such as the memory 128. The memory 128 is an external storage device, RAM, ROM, database, and/or a local memory (e.g., solid state drive or hard drive). The same or different non-transitory computer readable media may be used for the instructions and other data. The memory 128 may be implemented using a database management system (DBMS) and residing on a memory, such as a hard disk, RAM, or removable media. Alternatively, the memory 128 is internal to the processor 126 (e.g. cache).

The instructions for implementing the training or application processes, the methods, and/or the techniques discussed herein are provided on non-transitory computer-readable storage media or memories, such as a cache, buffer, RAM, removable media, hard drive or other computer readable storage media (e.g., the memory 128). Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU or system. Because some of the constituent system components and method steps depicted in the accompanying figures may be implemented in software, the actual connections between the system components (or the process steps) may differ depending upon the manner in which the present embodiments are programmed.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for application of a complex-valued neural network for a medical imaging system, the method comprising:
   scanning an internal region of a patient by the medical imaging system;
   applying the complex-valued neural network to scan data from the scanning and representing the internal region of the patient, the complex-valued neural network including one or more learned, complex-valued activation functions; and
   displaying an image having an indication output by the complex-valued neural network from the applying.

2. The method of claim 1 wherein scanning comprises scanning with the medical imaging system comprising a magnetic resonance scanner, wherein applying comprises inputting the scan data as complex values to the complex-valued neural network, and wherein displaying the image comprises displaying a magnetic resonance image.

3. The method of claim 2 wherein applying comprises applying with the complex-valued neural network having been trained for outputting values of multiple parameters for magnetic resonance fingerprinting, and wherein displaying the image comprises displaying the image for one of the parameters and displaying another image for another of the parameters.

4. The method of claim 1 wherein applying comprises applying with the complex-valued neural network having been trained for flow, Dixon, fingerprinting, or processing in k-space.

5. The method of claim 1 wherein applying comprises applying with the one or more learned, complex-valued activation functions each comprising a learned parameter for a relationship between real and imaginary components or between magnitude and phase components.

6. The method of claim 1 wherein applying comprises applying with the one or more learned, complex-valued activation functions comprising learned non-linearities.

7. The method of claim 1 wherein applying comprises applying with the one or more leaned, complex-valued activation functions comprising a machine-learned parameter in a two-dimensional complex grid.

8. The method of claim 7 wherein applying comprises applying with the machine-learned parameter comprising a machine-learned angle as a bias term for rotation in phase of a Cardioid function.

9. The method of claim 7 wherein applying comprises applying with the machine-learned parameter comprising a machine-learned mixing coefficient with shifts in the two-dimensional complex grid, a machine-learned kernel with two-dimensional vectors in the two-dimensional complex grid, or both in a kernel activation function.

10. The method of claim 9 wherein applying comprises applying the machine-learned mixing coefficient with shifts in the two-dimensional complex grid and the machine-learned kernel with two-dimensional vectors in the two-dimensional complex grid in the kernel activation function as a bivariate kernel activation function.

11. The method of claim 7 wherein applying comprises applying with the machine-learned parameter comprising a machine-learned parameter comprising a separable kernel of a kernel activation function, the separable kernel having a polar representation for complex numbers.

12. The method of claim 1 wherein applying the complex-valued neural network comprises applying a fully connected, dropout, batch-normalization, multi-dimensional convolution, average pooling, magnitude-max pooling, or magnitude transformation neural network.

13. The method of claim 1 wherein applying comprises applying with the one or more leaned, complex-valued activation functions comprising a ReLU with a learned rotation.

14. A medical imaging system for operating on complex-valued data, the medical imaging system comprising:
   a medical scanner configured to scan a patient and generate the complex-valued data from the scan;
   an image processor configured to apply the complex-valued data to a machine-learned model, the machine-learned model including a two-dimensional activation function with two dimensions being real and imaginary or magnitude and phase, at least one learned parameter of the two-dimensional activation function learned to relate between the two dimensions; and
   a display configured to display a medical image from an output of the application.

15. The medical imaging system of claim 14 wherein the two-dimensional activation function comprises a Cardioid activation function, and the at least one learned parameter comprises a rotation in the two dimensions.

16. The medical imaging system of claim 14 wherein the two-dimensional activation function comprises a kernel activation function, and the at least one learned parameter comprises a mixing coefficient in both of the two dimensions, a kernel in the two dimensions, or both.

17. The medical imaging system of claim 14 wherein the two-dimensional activation function comprises a kernel activation function, and the at least one learned parameter comprises a separable kernel in a polar representation.

18. A method for machine training in a complex-valued neural network, the method comprising:
   defining the complex-valued neural network with a Cardioid or kernel activation function, the Cardioid or kernel activation function having a learnable parameter in a real and imaginary or magnitude and phase grid;
   machine training, by a machine, the complex-valued neural network, the machine training including training the learnable parameter; and
   storing the neural network as trained.

19. The method of claim 18 wherein defining comprises defining the Cardioid or kernel activation function as the Cardioid activation function with the learnable parameter comprising a rotation in the grid.

20. The method of claim 18 wherein defining comprises defining the Cardioid or kernel activation function as the kernel activation function with the learnable parameter comprising grid shifts in both directions of the grid, variance in both the directions, or both.

* * * * *